United States Patent [19]

Warriner

[11] Plant 3,998

[45] Dec. 21, 1976

[54] ROSE PLANT

[75] Inventor: William A. Warriner, Tustin, Calif.

[73] Assignee: Jackson & Perkins Company, Medford, Oreg.

[21] Appl. No.: 634,666

[22] Filed: Nov. 24, 1975

[51] Int. Cl.[2] ..... A01H 5/00

[52] U.S. Cl. ..... Plt./11

[58] Field of Search ..... Plt./11

*Primary Examiner*—Robert E. Bagwill

*Attorney, Agent, or Firm*—Klarquist, Sparkman, Campbell, Leigh, Hall & Whinston

CLAIM

A new and distinct cultivar of rose plant of the hybrid tea class, substantially as herein shown and described, characterized particularly as to novelty by the unique combination of its medium green, leathery textured foliage; vigorous upright and open habit of growth; flowers of 20 to 30 large round petals; flower color of Orient Pink, when protected from the sun before opening, darkening to Rose Opal when fully open.

1 Drawing Figure

The present invention relates to a new and distinct cultivar of rose plant of the hybrid tea class which was originated by me by crossing an unnamed cultivar with pollen from the cultivar Spellbinder, U.S. Plant Pat. No. 3,571.

The primary objective of this breeding was to produce a new rose cultivar of the hybrid tea class, possessing the strong photochemical reaction in the pigment of the flower of the pollen parent, but having different plant characteristics, flower form, and color. This objective was substantially achieved along with other desirable traits as evidenced by the following unique combination of characteristics which are outstanding in the new cultivar and which distinguish it from its parents as well as from all other cultivars of which I am aware:

1. A vigorous, upright, but open habit of growth.
2. Large, leathery foliage, similar to that of Spellbinder in shape and texture but of a generally lighter shade of green.
3. Flower form loosely imbricated to flat when fully open as compared to a tightly imbricated form in Spellbinder.
4. Petalage of approximately 20 to 30 petals.
5. Flower color is lighter when fully expanded and exposed to sunlight for several days than is the color of Spellbinder.
6. Little or no fragrance.

Asexual reproduction of this new cultivar by budding, as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development depicted in color as nearly true as it is reasonably possible to make the same in a color illustration of this character.

The following is a detailed description of my new rose cultivar with color terminology in accordance with Wilson's Horticultural Color Chart, except where ordinary dictionary significance of color is indicated.

Parentage: Seedling.

*Seed Parent.*—Unnamed cultivar.

*Pollen Parent.*—Spellbinder, U.S. Plant Pat. No. 3,571.

Classification:

*Botanical.*—Rosa hybrid.

*Commercial.*—Hybrid Tea.

FLOWER

Observations were made from specimens grown at Irvine, Calif., September 1975.

Blooming habit: Continuous.

Bud:

*Size.*—Approximately 1¼" when petals start to unfurl.

*Form.*—Pointed ovoid.

*Color.*—When sepals first divide—near Cardinal Red (822/1) overlayed near petal tip with Oxblood Red (00823/3). When quarter open—upper side of petals between Cardinal Red (822/1) and Rose Opal (022) generally near tip lightening irregularly to Rose Opal (022/1) and Rose Opal (022/3) near base. Petal base Canary Yellow (2); lower side of petals similar to upper side, but more uniformly Rose Opal (22/1).

*Sepals.*—Color: Outer surface near Scheeles Green (860/3) irregularly overlaid with Garnet Brown (00918/3). Inner surface—lighter than Scheeles Green (860/3) near edges; center area near Pod Green (061/1). Three appendaged sepals lightly appendaged. Two unappendaged sepals hairy edged.

*Receptacle.*—Color: Near Scheeles Green (860/3) irregularly overlaid with Garnet Brown (00918/3). Shape: funnel with parallel sides. Size: large. Surface: slightly glandular.

*Peduncle.*—Length: short. Surface: slightly glandular. Color: bronzy. Strength: stiff, erect.

*Opening.*—Petals fold out with very little curling or recurving.

Bloom:

*Size.*—Large. Average open size 5".

*Borne.*—Singly and several together.

*Stem.*—Long, strong.

*Form.*—Flat to high center when first open. Permanence: retains its form to the end.

*Petalage.*—Number of petals under normal conditions: 20–30.

*Color.*—Center of flower: Upper side of petals near Orient Pink (416). Outer edge of flower: near Rose Opal (022/1). Reverse side of petals near Porcelain Rose (620/2). Base of petals Canary Yellow (2). General tonality from a distance: a blend of Orient Pink (416) irregularly with Rose Opal (022/1) near outer petals.

*Variegations.*—As noted above.

*Discoloration.*—General tonality at end of first day usually more Orient Pink (416) than Rose Opal with reflections of Porcelain Rose (620/2) from lower side of petals. Third day: color changes to nearly all Rose Opal (022/1) and Rose Opal (022) or darker. Color changes only when flowers are on plant. As cut flowers (indoors) the color remains near Orient Pink (416).

*Fragrance.*—Slight.

Petals:

*Texture.*—Thick.

*Shape.*—Round.

*Form.*—Flat to tips slightly recurved.

*Arrangement.*—Informal. Petaloids in center, few.

*Persistence.*—Drop off cleanly.

*Lastingness.*—On the plant—long. As cut flower—long.

Reproductive parts:

*Anthers.*—Large. Color—yellow. Arrangement—regular around styles.

*Filaments.*—Color—reddish at base to light yellow at tip.

*Pollen.*—

*Styles.*—Color—reddish

*Stigmas.*—Color—light yellow.

PLANT

Form: Bush.

Growth: Vigorous, upright, branching.

Foliage: Number of leaflets on normal mid-stem leaves 5 or 7.

*Size.*—Large.

*Quantity.*—Normal.

*Color.*—New foliage—near Garnet Brown (00918/3). Old foliage—near Spinach Green (0960).

Leaflets:

*Shape.*—Oval pointed.

*Texture.*—Upper side—leathery.

*Edge.*—Serrated.

*Serration.*—Single, small.

*Petiole.*—(rachis) Color—green. Reddish on upper side. Underside—prickles.

*Stipules.*—Long, slightly glandular.

*Disease Resistance.*—Normal resistance to mildew under normal growing conditions at Irvine, Calif.

Wood:

*New Wood.*—Color—light green with Garnet Brown (00918/3) shadings. Bark—smooth.

*Old Wood.*—Color—brown. Bark—smooth.

Prickles:

*Quantity.*—On main stalks from base—many. On laterals from stalk—many.

*Form.*—Broad base, long, hooked downward.

*Color when young.*—Brown.

*Position.*—Irregular.

Small Prickles:

*Quantity.*—On main stalks—none. On laterals—none.

I claim:

1. A new and distinct cultivar of rose plant of the hybrid tea class, substantially as herein shown and described, characterized particularly as to novelty by the unique combination of its medium green, leathery textured foliage; vigorous upright and open habit of growth; flowers of 20 to 30 large round petals; flower color of Orient Pink, when protected from the sun before opening, darkening to Rose Opal when fully open.

* * * * *

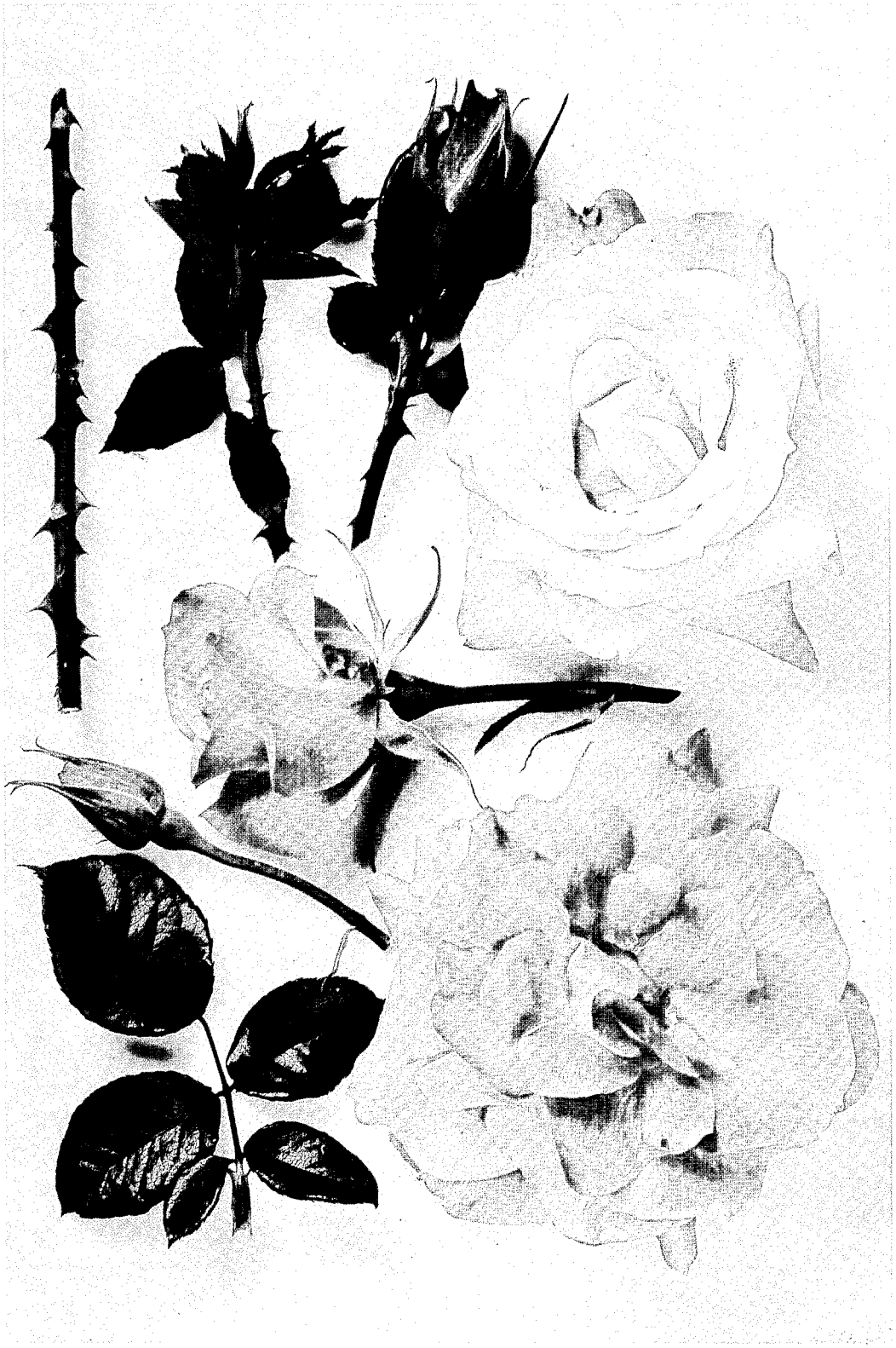

Dec. 21, 1976
W. A. WARRINER
ROSE PLANT
Filed Nov. 24, 1975
Plant Pat. 3,998